US00PP11260P

United States Patent [19]

Lane

[11] Patent Number: Plant 11,260

[45] Date of Patent: Mar. 7, 2000

[54] MUSCADINE GRAPE PLANT NAMED 'SCARLETT'

[75] Inventor: Ronald Paton Lane, Griffin, Ga.

[73] Assignee: University of Georgia Research Foundation, Inc., Athens, Ga.

[21] Appl. No.: 08/899,835

[22] Filed: Jul. 24, 1997

[51] Int. Cl.[7] ..... A01H 5/00

[52] U.S. Cl. ..... Plt./206

[58] Field of Search ..... Plt./47.2, 206

[56] References Cited

U.S. PATENT DOCUMENTS

P.P. 9,224 8/1995 Ison ..... Plt./47.2

P.P. 9,454 2/1996 Mortensen ..... Plt./47.2

P.P. 9,916 6/1997 Gargiulo ..... Plt./47.1

P.P. 10,434 6/1998 Cain ..... Plt./47.1

*Primary Examiner*—Howard J. Locker

*Assistant Examiner*—Kent L. Bell

*Attorney, Agent, or Firm*—Needle & Rosenberg, P.C.

[57] ABSTRACT

A new and distinct cultivar of the muscadine grape plant, *Vitis rotundifolia* Michx., which has an exceptionally flavorful berry, scoring higher in taste panel rankings than the current grapes that are produced commercially. The vines of this cultivar are vigorous, productive and tolerant to many diseases affecting muscadine grape plants.

1 Drawing Sheet

SUMMARY OF THE INVENTION

The present invention comprises a new and distinct plant cultivar of *Vitis rotundifolia* Michx. which has been given the name 'Scarlet'. The following traits have been repeatedly observed and are the most pronounced characteristics of this new cultivar when grown in Georgia, and which in combination distinguish it from existing cultivars:

1) Vigorous vine growth, high fruit yield, and good disease tolerance.

2) Pistillate flowers produced in abundance.

3) Large, reddish colored fruit.

4) High taste-panel rankings for flavor.

5) High percentage of dry stem scar on berries.

BRIEF DESCRIPTIONS OF THE DRAWINGS

The accompanying two color photographs show representative sections of a typical specimen of the new cultivar.

The top photograph shows a large section of a mature vine, typical of the species, showing leaves and fruits.

The bottom photograph is a more detailed view of several clusters of ripe berries, obtained by clipping away some foliage. Both photographs show the colors as it is reasonably possible to obtain in colored reproductions of this type. Actual leaf and fruit colors may differ from leaf and fruit colors in the photograph due to light reflectance.

DETAILED DESCRIPTION

In the following description, color references are made to The Royal Horticultural Society Colour Chart except where general terms of ordinary dictionary significance are used.

BACKGROUND OF THE INVENTION

The muscadine grape, *Vitis rotundifolia* Michx., is a popular fresh fruit grown in the Southeastern United States. In the Georgia climate, it ripens in early autumn when few other fruits are in season. The berries are large, as compared to other grape species, and are borne in clusters of 5–7 berries. When fully ripe, the berries on existing cultivars are medium brown with slightly raised lenticels, giving a somewhat mottled appearance. 'Summit' (unpatented) is a muscadine grape cultivar introduced in 1977 (Lane, 1977) for the fresh fruit market in the Southeastern United States. It was developed from a cross of the cv. 'Fry' (unpatented) and a germplasm, Ga. 29–49 made by Mr. B. O. Fry in 1965. The original seedling from this cross was selected in 1971 and propagates were made available to growers begining in 1974, under the experimental number 'Ga. 37–40'. 'Summit's distinguishing features were its relatively large sized berry and a greater sweetness than existing cultivars at the time of its release. 'Triumph' (unpatented) is another selection from the same cross made by Mr. Fry in 1965. The original seedling was identified in 1971, and the cultivar has been grown commercially for over a decade (Lane, 1980). Two distinguishing characteristics of 'Triumph' are its prolific pollen production, making it an excellent planting adjacent to pistillate cultivars, and the high percentage of its berries which separate with a dry stem scar (i.e. no tear in the berry at the point of detachment from the pedicel). Despite the distinguishing characteristics of 'Summit' and 'Triumph', their smaller berry size and lack of improved taste has limited their commercial acceptance over the standard, cv. 'Fry'. Thus, there has been a need to develop a new cultivar that has a large berry size and a high level of sweetness which also retains important agronomic characteristics such as vigorous growth, high yield, and disease tolerance. Additionally, there is a need to develop a muscadine grape plant cultivar with a relatively dry stem scar to minimize berry damage for the fresh fruit market.

Origin of the Invention

The plant of this invention, 'Scarlett', was developed from an organized, scientifically designed breeding program conducted at the University of Georgia Experiment Station at Griffin, Ga. 'Scarlett' originated from a sibling cross between 'Summit' and 'Triumph' made in 1981. The seedling was selected from a progeny of 23, and testing of the agronomic characteristics began in 1993 at two independent sites in Georgia. The new cultivar was asexually reproduced from cuttings taken from the original seedling and the new cultivar has been tested under the experimental designation GA 35-9-1. The unique features of the new cultivar have been retained.

Methods of Asexual Reproduction

'Scarlett' was asexually reproduced in Griffin, Ga. utilizing standard mist propagation techniques as described in Goode and Lane, (1983). No hormones were used. Four-node softwood cuttings were placed in a 50% sand and 50% peat moss medium.

Other methods of asexual reproduction are possible. One alternate method comprises layering, wherein the current season's growth is placed in a trench 4–6" deep at the base of the mother plant, still attached to the mother vine, and covered with moist material such a sphagnum moss. Rooted cuttings from the material in the trench can then be separated from the mother plant during the following dormant season.

Alternatively, rooting of hardwood cuttings is more difficult, but possible. Tissue culturing, or in vitro micropropagation, using meristems or nodes is another means of propagation, as is somatic embryogenesis.

Plant Characteristics

Vines: The vines of 'Scarlett' grow vigorously, i.e. the growth of lateral canes on mature vines is at least 48 inches per growing season, while 36 inches per growing season is typical for the species. The vines typically fill a twenty foot single-wire trellis by the end of the first growing season in Georgia, and the vines fill out a two-wire parallel trellis (i.e. 40 foot trellis) during the second growing season in Georgia. The trunk caliper measurement at 12 inches above the soil line averages 1.8 inches for a typical five-year old vine.

Canes: Lateral canes are semi-drooping and usually grow four feet or more in a season in Georgia. The color of mature canes is greyish brown and the bark is smooth. Cane diameter is 0.2 to 0.5 inches. Internode length ranges from 1 to 3 inches. Tendrils, averaging 5.2 inches in length, are unbranched and discontinuous along the nodes.

Foliage: Leaves average 3.5 inches in length and 3.8 inches in width. The leaves are circular with broadly toothed margins and glabrous on both upper and lower surfaces. Mature upper leaf surfaces are dark green (137A, Royal Horticultural Society colour chart) and somewhat dull, while the lower leaf surfaces are light green (138A, Royal Horticultural Society colour chart) and shiny. Petiole length equals or slightly exceeds the blade middrib length and the petiole sinus is open.

Flowers: The flowers are pistillate. The petals are white and small (with the inflorescence less than 0.25 inches in diameter), which is typical for the species. The nonfunctional greenish to cream-colored anthers are supported on very short filaments at the base of the ovary. The flowers are short lived, lasting approximately three to five days. 'Scarlet' typically blooms from May 20$^{th}$ through June 10$^{th}$ at Griffin, Ga. Successful pollination of 'Scarlett' has been accomplished with 'Carlos', 'Cowart', 'Nesbitt', 'Tara', and 'Triumph'.

Fruit: The vines produce large, reddish colored fruit, which ripen in a 2– to 3–week period beginning around September 10th in Griffin, Ga. At maturity, the berries weigh approximately 11 g each and average 17.3% soluble solids. The berries are slightly elongated and range from ⅞ to 1¼ inches in diameter, containing an average of 3.3 seeds per berry. The berries have conspicuous lenticels giving them a somewhat mottled appearance. The berries separate from the pedicel with a relatively dry stem scar, i.e. less than 25% of the berries are torn at the point of detachment from the pedicel. The reddish color of the 'Scarlet' fruit, based on The Royal Horticultural Society of London Colour Chart falls into the greyed-red group, 182-A. This fruit color is distinct from the bronze fruit of 'Triumph', the greenish-bronze fruit of 'Fry', and the reddish bronze fruit of 'Summit'. A comparison of the important fruit characteristics (size, sweetness, % dry stem scar, flavor rating) and overall yield are presented in Table 1; these observations have been made annually for three years, and the traits have been retained.

The taste panel ratings in Table 1 reflect an overall flavor rating, in which the panelists rated the fruit on a scale of 1 to 10, where 1 was "poor flavor" and 10 was "excellent flavor".

TABLE 1

Characteristics and Yield of 'Scarlett' campared to three fresh market muscadine grape cultivars at Experiment, Georgia, 1993–95.

| Cultivar | Flower type[1] | Berry Wt. (g) | Soluble solids concn (%) | Dry stem scar (%)[2] | Flavor rating[3] | Yield (kg/vine) |
|---|---|---|---|---|---|---|
| Scarlett | P | 11.1 a[4] | 17.3 b | 78 a | 8.2 a | 34.7 a |
| Fry | P | 10.9 a | 16.6 b | 53 c | 6.6 b | 27.2 b |
| Summit | P | 9.3 b | 19.1 a | 67 b | 6.4 b | 33.3 a |
| Triumph | SF | 7.9 b | 17.7 b | 78 a | 5.8 b | 20.8 c |

[1]Flower type: SF = self-fertile, P = pistillate.
[2]Percentage of berries not torn at point of detachment from pedicel.
[3]Flavor ratings: 1 = poor, 2 = fair, 5 = good, 8 = very good, 10 = excellent.
[4]Mean separation by Duncan's multiple range test, P = 0.05. (Steel, R. G. D. and J. H. Torrie, 1980, "Principles and Procedures of Statistics", Second Ed.; McGraw-Hill, Inc., pp. 187–188.)

What is claimed is:

1. A new and distinct muscadine grape plant named 'Scarlett', substantially as herein illustrated and described, characterized by its exceptionally flavorful grape, vigorous vine growth and high fruit yield, good disease tolerance, abundant pistillate flowers, large reddish colored fruit, and a high percentage of dry stem scar on berries.

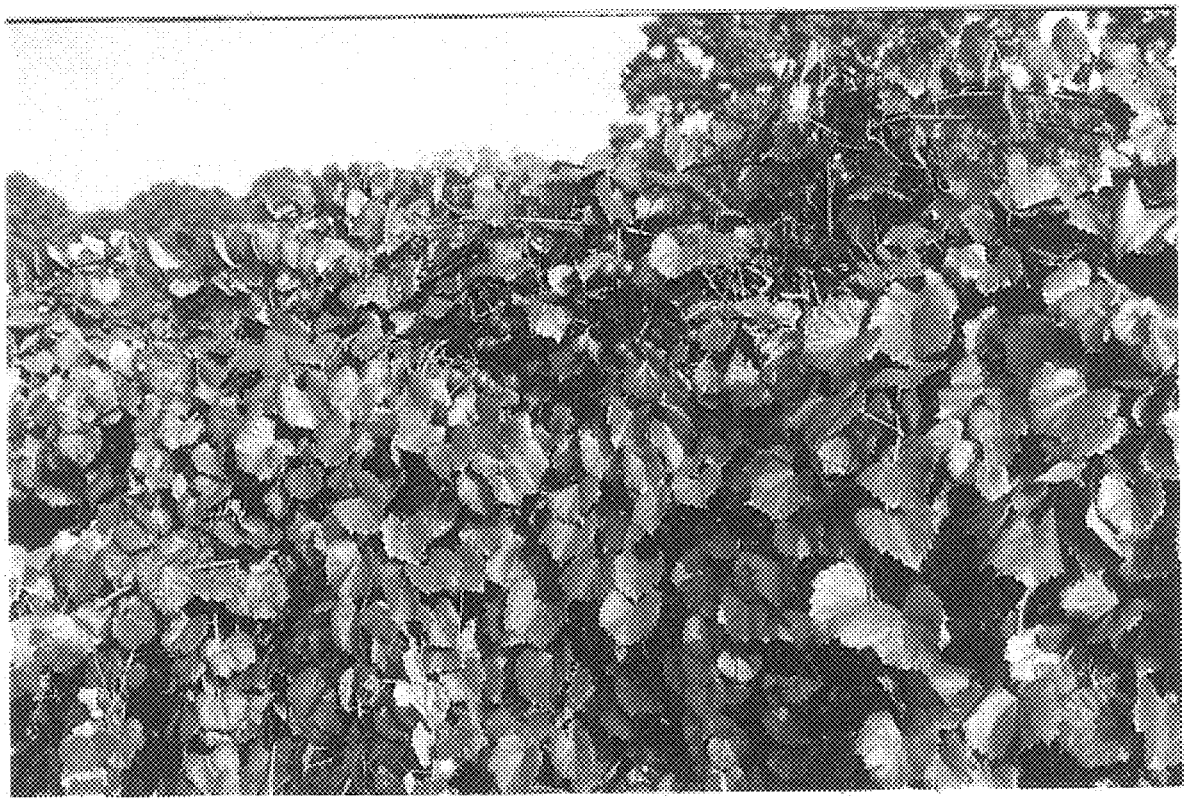
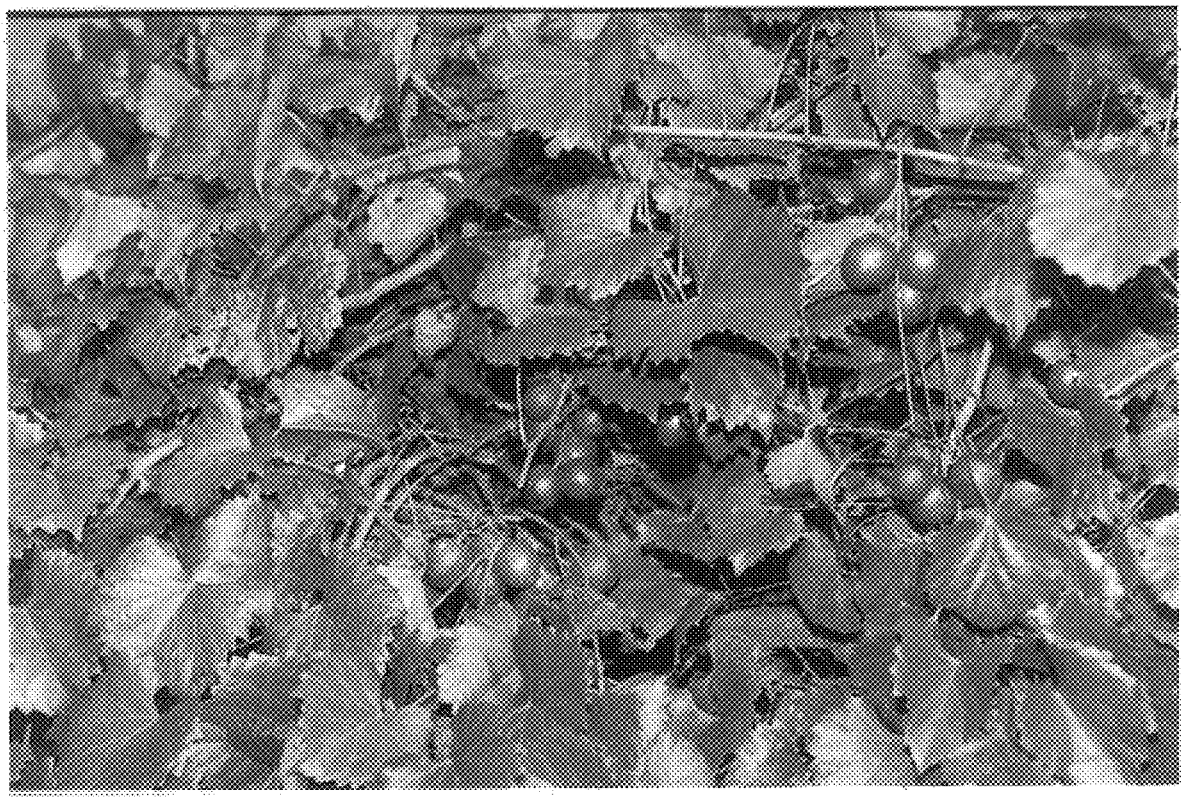

* * * * *